United States Patent [19]
Hofheinz

[11] 4,042,597
[45] Aug. 16, 1977

[54] PREPARATION OF 2-(2-HYDROXY-2-PROPYL)-1-METHYL-5-NITROIMIDAZOLE

[75] Inventor: Werner Hofheinz, Bottmingen, Switzerland

[73] Assignee: Hoffmann-La Roche Inc., Nutley, N.J.

[21] Appl. No.: 668,899

[22] Filed: Mar. 22, 1976

[30] Foreign Application Priority Data

Apr. 4, 1975  Switzerland ........................ 4291/75
Jan. 23, 1976  Switzerland ........................ 826/76

[51] Int. Cl.$^2$ .......................................... C07D 233/94
[52] U.S. Cl. ................................................ 548/339
[58] Field of Search ............................ 260/309, 618 C

[56] References Cited
U.S. PATENT DOCUMENTS

| 2,447,414 | 8/1948 | Kosmin et al. | 260/618 C |
| 3,402,205 | 9/1968 | Gregory | 260/618 C |
| 3,555,101 | 1/1971 | Buysch et al. | 260/618 C |
| 3,567,786 | 3/1971 | Bostian et al. | 260/618 C |
| 3,794,642 | 2/1974 | Kress | 260/618 C |

OTHER PUBLICATIONS

Kress et al., *J. Heterocyclic Chem.* 1972, vol. 9, 1161–1164.
Russell et al., *J. Org. Chem.*, 1967, vol. 32, pp. 137–146.
Raphael et al., *Advances in Organic Chemistry Methods and Results* vol. 5, pp. 2 and 3, N. Y., Interscience-Wiley, 1965.

*Primary Examiner*—Natalie Trousof
*Attorney, Agent, or Firm*—Samuel L. Welt; Bernard S. Leon; R. Hain Swope

[57] ABSTRACT

A method for preparing 2-(2-hydroxy-2-propyl-1-methyl-5-nitroimidazole by the autoxidation of 1-methyl-2-isopropyl-5-nitroimidazole is disclosed.

6 Claims, No Drawings

PREPARATION OF 2-(2-HYDROXY-2-PROPYL)-1-METHYL-5-NITROIMIDAZOLE

BACKGROUND OF THE INVENTION 2-(2-Hydroxy-2-propyl)-1-methyl-5-nitroimidazole is a known compound useful for the treatment of trichomoniasis and amoebiasis in human. The subject compound and its preparation are described in U.S. Pat. No. 3,652,579. The preparation described therein, however, is protracted and therefore inefficient for the production of 2-(2-hydroxy-2-propyl)-1-methyl-5-nitroimidazole in large amounts for commercial use. In accordance with the present invention, a method has been found for the preparation of 2-(2-hydroxy-2-propyl)-1-methyl-5-nitroimidazole which is both efficient and suitable for commercial production.

DETAILED DESCRIPTION OF THE INVENTION

In accordance with the present invention, 2-(2-hydroxy-2-propyl)-1-methyl-5-nitroimidazole is prepared in a single step reaction with good yield by the autoxidation of 1-methyl-2-isopropyl-5-nitroimidazole in the presence of a base. 1-Methyl-2-isopropyl-5-nitroimidazole is a known compound described in U.S. Pat. No. 3,634,446.

The process of the present invention is carried out in the presence of a dipolar aprotic solvent such as, for example, hexametapol, i.e. hexamethylphosphoric triamide, dimethylformamide, dimethylacetamide, dimethoxyethane, dimethylsulfoxide and the like. Preferred solvents are hexametapol and dimethylformamide.

The process of the present invention is further carried out at a temperature between about 50° and about −25° C., preferably between about 0° and −25° C. The temperature will vary, however, with the particular solvent being utilized and can, in principle, be either below or above the range given, depending on the solvent chosen. For example, wherein hexametapol is utilized, the temperature range is preferably between −15° and −25° C. As a general proposition, the yield of 2-(2-hydroxy-2-propyl)-1-methyl-5-nitroimidazole will increase when temperatures in the lower part of the range are utilized.

The oxidation agent utilized in the preparation of 2-(2-hydroxy-2-propyl)-1-methyl-5-nitroimidazole in accordance with the present invention may be either air or pure oxygen which are conducted through the reaction mixture.

The base utilized to catalyze the oxidation reaction described herein is a strong base, e.g. an alkali metal hydroxide such as, for example, sodium hydroxide or potassium hydroxide, an alkali metal alcoholate such as, for example, sodium methylate, sodium ethylate, sodium tert.amylate or potassium tert. butylate, sodium amide or the like. The base may be added to the reaction mixture per se, i.e. as a powder or crystals or in solution in a suitable solvent. Suitable solvents include, for example, water, lower alcohols, e.g. tert. butanol, ethers, e.g. diethyl ether or dimethoxyethane, hydrocarbons, preferably aromatic hydrocarbons, e.g. toluene, and liquid ammonia. Although the amount of base may vary over a wide range, optimum yields of 2-(2-hydroxy-2-propyl)-1-methyl-5-nitroimidazole are obtained when from about 0.1 to about 2 moles of base are present for each mole of 1-methyl-2-isopropyl-5-nitromidazole present as starting material. It is further preferred to add the base in portions as the reaction proceeds rather than all at the beginning.

Although not absolutely required, it is preferred in accordance with the present invention to include in the reaction mixture a suitable reducing agent to reduce the hydroperoxide intermediate to the desired alcohol thereby optimizing the yields. Suitable reducing agents include, for example, phosphosites, phosphines, sulfides and the likewith triethylphosphite being particularly preferred. When a reducing agent is utilized, it is present in from about 0.5 to about 1.5, preferably from about 1.0 to about 1.3 molar equivalents based on the starting material.

The process in accordance with the present invention has been found to produce crude yields of up to about 90% of 2-(2-hydroxy-2-propyl)-1-methyl-5-nitroimidazole. The crude mixture can be further purified by procedures well known in the art, such as, for example, chromatography, recrystallization or sublimation.

The following Examples further illustrate the present invention. Unless otherwise noted, all temperatures are in degrees centigrade:

EXAMPLE 1

A total of 11.2 ml of triethylphosphite and 5 ml of a 47.5% aqueous solution of potassium hydroxide were added to a solution of 8.5 g of 1-methyl-2-isopropyl-5-nitroimidazole in 50 ml of hexametapol while cooling in an ice-bath. The solution was subsequently vigorously stirred for 12 hours at room temperature and for 6 hours at 40° while passing dry oxygen through the solution. The resulting mixture was poured into a mixture of 250 ml of ice-water and 60 of 1-N hydrochloric acid and the aqueous solution extracted three times with 150 ml portions of ether. The combined ether extracts were washed with a small amount of water and evaporated on a rotary evaporator. 2.8 Grams of 2-(2-hydroxy-2-propyl)-1-methyl-5-nitroimidazole, melting point 106°–108° crystallized upon the addition of 50 ml of water. A further 0.5 g (melting point 105°–108°) was obtained upon concentration of the mother liquor. The total yield was 3.3 g (35.7%).

EXAMPLE 2

A total of 11.2 ml of triethylphosphite and 6 g of powdered potassium hydroxide were added to a solution of 8.5 g of 1-methyl-2-isopropyl-5-nitroimidazole in 40 ml of hexametapol while cooling in an ice-bath. While the solution was further cooled with ice, oxygen was conducted through the solution with vigorous stirring. After 2.5 hours, 6.1 ml of glacial acetic acid were added and the mixture was then poured into 600 ml of water and extracted four times with 150 ml portions of ether. The ether extracts were washed with a small amount of water, evaporated on a rotary evaporator and finally dried at 85°/0.5 Torr. The residue was crystallized from 15 ml of isopropyl ether. There were obtained 2.0 g of 2-(2-hydroxy-2-propyl)-1-methyl-5-nitroimidazole, melting point 102°–107°. The yield was 21.6%.

EXAMPLE 3

A total of 45 ml of a 2.25-N solution of sodium tert.amylate in toluene and 11.2 ml of triethylphosphite were added to a solution, cooled to −15°, of 8.5 g of 1-methyl-2-isopropyl-5-nitroimidazole in 85 ml of dimethylformamide. A strong oxygen stream was conducted through this mixture for 6 hours at a temperature of −10° to −15° while stirring vigorously. The mixture was then neutralized by the addition of 45 ml of 2-N hydrochloric acid and concentrated on a rotary evaporator at 50°/12 Torr. The residue was taken up in 250 ml of water and the aqueous solution extracted 3 times with 250 ml portions of dichloromethane. The combined dichloromethane extracts were washed with a small amount of water and concentrated to dryness. The residue was then taken up in ethyl acetate and chromatographed on 600 g of silica gel with ethyl acetate. After evaporation of the solvent on a rotary evaporator and crystallization from isopropyl ether, there were obtained 2.2 g of 2-(2-hydroxy-2-propyl)-1-methyl-5-nitroimidazole, melting point 106°–108°. The yield was 23.8%.

EXAMPLE 4

A total of 22.3 g of potassium were dissolved in 450 ml of tert.-butanol with vigorous stirring and the solution heated to reflux. After the addition of 300 ml of dimethylformamide, the mixture was cooled to −15° and treated with a solution of 42.5 g of 1-methyl-2-isopropyl-5-nitroimidazole in 60 ml of triethylphosphite and 150 ml of dimethylformamide. Dry oxygen was conducted through the mixture for 5 hours at −15° with vigorous stirring. The mixture was then poured into a mixture of 1.5 liter of ice-water and 50 ml of 36% hydrochloric acid and extracted 6 times with 400 ml portions of ether. The combined ether extracts were washed twice with 250 ml portions of water and evaporated. The crude 2-(2-hydroxy-2-propyl)-1-methyl-5-nitroimidazole (33.8 g; 72.7%) was purified by recrystallization from 150 ml of water. There were obtained 15.6 g of pure product, melting point 105°–108°. Crystallization of the mother liquor from isopropyl ether yielded a further 8.6 g, melting point 103°–106° (total yield 52%).

EXAMPLE 5

A total of 21.5 g of potassium were dissolved in 450 ml of tert.-butanol with vigorous stirring and the solution heated to reflux. 300 ml of hexametapol were added to the cooled solution. The mixture was then cooled to −25°, a solution of 42.5 g of 1-methyl-2-isopropyl-5-nitroimidazole in 60 ml of triethylphosphite and 150 ml of hexametapol was added and dry oxygen was conducted through the mixture for 5 hours at −20° to −25° with vigorous stirring. The mixture was poured into a mixture of 1.5 liter of ice-water and 45 ml of 36% hydrochloric acid and extracted six times with 400 ml portions of ether. The combined ether extracts were washed twice with 250 ml portions of water and evaporated. The crude 2-(2-hydroxy-2-propyl)-1-methyl-5-nitroimidazole (40.5 g; 87%) was purified by crystallization from 300 ml of water. There were obtained 30.2 g of pure 2-(2-hydroxy-2-propyl)-1-methyl-5-nitroimidazole, melting point 106°–108° and a second crop of 4.2 g, melting point 102°–105° (total yield 74%).

EXAMPLE 6

A total of 100 ml of triethylphosphite and 6.8 g of sodium ethylate were added to a solution, pre-cooled to −10°, of 85 g of 1-methyl-2-isopropyl-5-nitroimidazole in 500 ml of dimethylformamide. While the solution was further cooled with an ice/sodium chloride bath, dry oxygen was conducted through the solution with vigorous stirring. In so doing, the solution warmed to +5° to +8°. This temperature was maintained during the entire duration of the reaction by corresponding cooling. At intervals of 0.5 hour, 6.8 g aliquots of sodium ethylate were added to the mixture. After 4.5 hours and the addition of a total of 61.2 g of sodium ethylate, the dark-colored solution was poured into 3 liters of water and extracted four times with 1 liter portions of ethyl acetate. The ethyl acetate extracts were combined, washed twice with 0.5 liter portions of water and evaporated. The residue consisted of 76.1 g (81.8%) crystalline 2-(2-hydroxy-2-propyl)-1-methyl-5-nitroimidazole which upon recrystallization from 400 ml of isopropyl ether yielded 64.6 g of pure product, melting point 107°–108° (69.6%).

EXAMPLE 7

A total of 2.3 g of sodium were dissolved in 200 ml of liquid ammonia to which had previously been added a spatula-tip of ferric chloride. To the resulting sodium amide suspension was added a solution of 8.5 g of 1-methyl-2-isopropyl-5-nitro-imidazole and 11 ml of triethylphosphite in 50 ml of absolute tetrahydrofuran and a strong oxygen stream was conducted through the well-stirred mixture for 1 hour. Thereafter, 10 ml of ethanol were added and the ammonia allowed to evaporate off. The residue was poured into 400 ml of water, acidified with 3-N hydrochloric acid and extracted four times with 150 ml portions of ethyl acetate. The combined ethyl acetate extracts were washed with a small amount of water and evaporated. There was obtained a solid residue weighing 7.3 g and consisting of a 1:1 mixture of 1-methyl-2-isopropyl-5-nitroimidazole and 2-(2-hydroxy-2-propyl)-1-methyl-5-nitroimidazole.

I claim:
1. A process for the preparation of 2-(2-hydroxy-2-propyl)-1-methyl-5-nitroimidazole which comprises autoxidizing 1-methyl-2-isopropyl-5-nitroimidazole in a dipolar aprotic solvent in the presence of a strong base and a reducing agent comprising triethylphosphite.

2. A process in accordance with claim 1 wherein from about 0.1 mole to about 2 moles of said base are present for each mole of 1-methyl-2-isopropyl-5-nitroimidazole utilized.

3. A process in accordance with claim 1 wherein said reaction is carried out at a temperature between about 0° C. and about −25° C.

4. A process in accordance with claim 1 wherein said solvent is selected from the group consisting of hexametapol, dimethylformamide, dimethylacetamide, dimethoxyethane and and dimethylsulfoxide.

5. A process in accordance with claim 4 wherein said solvent is hexametapol and said reaction is carried out at a temperature between about −15° C. and about −25° C.

6. A process in accordance with claim 4 wherein said solvent is dimethylformamide.

* * * * *